United States Patent
Ahmed et al.

(10) Patent No.: US 11,547,314 B2
(45) Date of Patent: Jan. 10, 2023

(54) OPTICAL COHERENCE TOMOGRAPHY SYSTEM

(71) Applicant: DOTTER INC., Incheon (KR)

(72) Inventors: Yosuf Syed Ahmed, Incheon (KR); Juhyun Chung, Incheon (KR); Jong Woo Han, Incheon (KR); Hyung Il Kim, Incheon (KR)

(73) Assignee: DOTTER INC., Incheon (KR)

( * ) Notice: Subject to any disclaimer, the term of this patent is extended or adjusted under 35 U.S.C. 154(b) by 385 days.

(21) Appl. No.: 16/759,797

(22) PCT Filed: Nov. 28, 2017

(86) PCT No.: PCT/KR2017/013715
§ 371 (c)(1),
(2) Date: Apr. 28, 2020

(87) PCT Pub. No.: WO2019/107581
PCT Pub. Date: Jun. 6, 2019

(65) Prior Publication Data
US 2021/0177282 A1    Jun. 17, 2021

(51) Int. Cl.
*A61B 5/00*    (2006.01)
*A61B 5/026*    (2006.01)
(Continued)

(52) U.S. Cl.
CPC ........ *A61B 5/0261* (2013.01); *A61B 1/00117* (2013.01); *A61B 5/4881* (2013.01); *A61B 5/6852* (2013.01); *G01B 9/02091* (2013.01)

(58) Field of Classification Search
CPC .......... A61B 1/00117; A61B 2562/228; A61B 5/0066; A61B 5/0084; A61B 5/0261;
(Continued)

(56) References Cited

U.S. PATENT DOCUMENTS

2004/0254474 A1    12/2004    Seibel et al.
2007/0015969 A1    1/2007    Feldman et al.
(Continued)

FOREIGN PATENT DOCUMENTS

JP    2008-504557 A    2/2008
JP    2008-541989 A    11/2008
(Continued)

OTHER PUBLICATIONS

International Search Report dated Aug. 16, 2018 for International Application No. PCT/KR2017/013715, 6 pages with English translation.

*Primary Examiner* — Mark D Remaly
(74) *Attorney, Agent, or Firm* — MH2 Technology Law Group LLP (57) ABSTRACT

Disclosed is an optical coherence tomography (OCT) system according to an exemplary embodiment of the present disclosure. The OCT system may include: a light source unit generating light; an optical interferometer including an optical coupler splitting the light generated by the light source unit into first distribution light and second distribution light, a reference arm reflecting the first distribution light, a sample arm reflecting the second distribution light, and an optical detector detecting the light reflected by the reference arm and the sample arm; an OCT catheter including an optical fiber having a shape in which the optical fiber is insertable into at least a part of a human body and is rotatable and discharging the light to a tissue and collecting OCT data for the tissue; an OCT engine including a processor and a storage unit and processing the OCT data collected by the OCT catheter; and an OCT controller connected to a proximal end of the OCT catheter and controlling rotation of the OCT catheter.

18 Claims, 9 Drawing Sheets

(51) Int. Cl.
*G01B 9/02091* (2022.01)
*A61B 1/00* (2006.01)

(58) Field of Classification Search
CPC ... A61B 5/4881; A61B 5/6852; A61B 5/6876; G01B 9/02091
See application file for complete search history.

(56) References Cited

U.S. PATENT DOCUMENTS

| | | |
|---|---|---|
| 2012/0245569 A1 | 9/2012 | Papac et al. |
| 2014/0142427 A1 | 5/2014 | Petroff |
| 2015/0173605 A1 | 6/2015 | Wheatley et al. |
| 2015/0226537 A1* | 8/2015 | Schorre .............. G01B 9/02063 356/479 |

FOREIGN PATENT DOCUMENTS

| | | |
|---|---|---|
| JP | 2014-509909 A | 4/2014 |
| JP | 2017-500119 A | 1/2017 |

* cited by examiner

OPTICAL COHERENCE TOMOGRAPHY SYSTEM

TECHNICAL FIELD

The present disclosure relates to a medical device, and more particularly, to an optical coherence tomography (OCT) system.

BACKGROUND ART

Since medical technology is an act of treating diseases and saving lives of people, large technological investment and research for the medical technology have been made. As a result of the technological investment and research, an internal image of a human body is acquired through medical equipment to achieve accurate diagnosis for a patient and the resulting treatment. The medical equipment capable of acquiring the internal image of the human body includes X-ray imaging equipment, magnetic resonance imaging (MRI) equipment, computer tomography (CT) equipment, and ultrasound imaging equipment. The equipment may be classified into equipment (i.e., non-invasive imaging equipment) for photographing the inside of the human body from the outside of the human body.

For example, in order to ensure accuracy of imaging for fine blood vessel tissues such as a cardiovascular field and tissues which continuously move, various types of equipment have been developed, which is related to acquisition of an internal image of the human body in an invasive scheme. Since the invasive-scheme imaging equipment is inserted into the human body and photographs the inside of the human body, for example, the invasive-scheme imaging equipment may be used for diagnosing an anatomical structure (e.g., stenosis) inside the blood vessel.

As the invasive imaging equipment, intravascular ultrasound (IVUS) imaging equipment exists. The intravascular ultrasound (IVUS) imaging equipment may evaluate intravascular atheromatous plaque characteristics by overcoming a limit of coronary angiography (a method for evaluating an internal blood vessel by injecting a contrast medium into the blood vessel) used to diagnose the anatomical structure and stenosis of coronary artery. In the intravascular ultrasound imaging scheme, a rotating ultrasound generating device is attached to an end of a fine tube capable of entering the inside of the blood vessel to observe a stenosis degree of the blood vessel and a state of the atheromatous plaque.

In recent years, an optical coherence tomography (OCT) system has been developed, which has a higher resolution than the IVUS imaging equipment to enable evaluation of a micro structure (e.g., a micro structure of coronary atheromatous plague in the human body, which is difficult to observe by means of the IVUS imaging equipment.

The OCT system is an optical tomography device that generally images a cross section of a body tissue by using a light source of a near infrared (e.g., wavelength 0.6 to 1.3 µm) area. The OCT technology is evaluated as new imaging technology which is studied in order to complement a human hazard issue, a price issue, and a measurement resolution issue of the existing invasive schemes of measurement equipment such as computer tomography (CT), ultrasound imaging, and magnetic resonance imaging equipment.

The OCT technology has a higher resolution than the existing IVUS technology and has many advantages including an advantage that the inside of a target object may be photographed by a non-cutting scheme, an advantage that real-time tomography imaging is available with development of Fourier-domain OCT, and an advantage that small and low-price devices can be fabricated.

The OCT technology is technology that performs 3D imaging for the inside of a living body by using a coherence phenomenon of light and when the OCT technology is invasively used, for example, a catheter formed by an optical fiber is inserted into the blood vessel to acquire an image of the inside of a blood vessel wall. In this case, the OCT technology may be utilized as various forms such as stenting, discovery of macrophage, evaluation of usefulness of medication, discovery of thrombosis, discovery of coronary atheromatous plaque, and/or evaluation of a coronary artery lesion. Moreover, when the OCT technology is non-invasively used, for example, since a high-resolution image may be acquired through tomography for the cornea and the retina, the OCT technology may be used as a measurement device for ophthalmology and used as a measurement device for dermatology such as non-invasive blood glucose measurement and/or diagnosis for skin and scalp.

As the advantage of the OCT technology is utilized, the OCT technology may also be applied to various industrial fields including polymer characteristic analysis, thin film thickness measurement, wiper scanning, fingerprint detection, and measurement for MEMS equipment.

As described above, at present, various researches for OCT technology are made and for example, Prior U.S. Pat. No. 6,445,939 presents a technical feature for an ultra-small optical probe used in the OCT system and another Prior U.S. Pat. No. 8,831,321 presents a technical feature for detecting a side branch for the blood vessel by utilizing the OCT system, and yet another Prior U.S. Pat. No. 9,069,396 presents a technical feature for an OCT controller including a joystick type user input unit.

SUMMARY OF THE INVENTION

The present disclosure has been contrived according to the aforementioned background art and has been made in an effort to develop an OCT system capable of guaranteeing stability and reliability for photographing through high-speed rotation.

Further, the present disclosure has also been made in an effort to develop an OCT system for enhancing user convenience.

An exemplary embodiment of the present disclosure provides an OCT system. The OCT system may include: a light source unit generating light; an optical interferometer including an optical coupler splitting the light generated by the light source unit into first distribution light and second distribution light, a reference arm reflecting the first distribution light, a sample arm reflecting the second distribution light, and an optical detector detecting the light reflected by the reference arm and the sample arm; an OCT catheter including an optical fiber having a shape in which the optical fiber is insertable into at least a part of a human body and is rotatable and discharging the light to a tissue and collecting OCT data for the tissue; an OCT engine including a processor and a storage unit and processing the OCT data collected by the OCT catheter; and an OCT controller connected to a proximal end of the OCT catheter and controlling rotation of the OCT catheter.

According to an exemplary embodiment of the present disclosure, an OCT system can be derived, which is capable of guaranteeing stability and reliability for photographing through high-speed rotation.

According to an exemplary embodiment of the present disclosure, user convenience of users who use the OCT system can be maximized.

BRIEF DESCRIPTION OF THE DRAWINGS

Some of embodiments are illustrated in the accompanying drawings so as to appreciate features of the mentioned disclosed contents with reference to the following embodiments through detailed and more concrete description. Further, it is intended that like reference numerals in the drawing denote the same or similar function throughout several exemplary embodiments. However, the accompanying drawings just illustrate only specific typical embodiments of the disclosed contents and are not considered to limit the scope of the present disclosure and it should be noted that other embodiments having the same effect can be sufficiently recognized.

DETAILED DESCRIPTION

Various embodiments and/or aspects will be now disclosed with reference to drawings. In the following description, for the purpose of a description, multiple detailed matters will be disclosed in order to help comprehensive appreciation of one or more aspects. However, those skilled in the art will recognize that the aspect(s) can be executed without the detailed matters. In the following disclosure and the accompanying drawings, specific exemplary aspects of one or more aspects will be described in detail. However, the aspects are exemplary and some of various methods in principles of various aspects may be used and the descriptions are intended to include all of the aspects and equivalents thereof.

Various aspects and features will be presented by a system which can include multiple devices, components, and/or modules. It should also be appreciated and recognized that various systems can include additional apparatuses, components, and/or modules and/or that the various systems cannot include all of apparatuses, components, modules, and the like discussed in association with the drawings.

In "embodiment", "example", "aspect", "illustration", and the like used in the specification, it may not be construed that a predetermined aspect or design which is described is more excellent or advantageous than other aspects or designs. 'Component', 'module', 'system', 'interface', and the like which are terms used below generally mean computer-related entities and mean, for example, hardware, a combination of the hardware and software, and the software.

The term "or" is intended to mean not exclusive "or" but inclusive "or". That is, when not separately specified or not clear in terms of a context, a sentence "X uses A or B" is intended to mean one of the natural inclusive substitutions. That is, the sentence "X uses A or B" may be applied to all of the case where X uses A, the case where X uses B, or the case where X uses both A and B. Further, it should be understood that the term "and/or" used in the specification designates and includes all available combinations of one or more items among enumerated related items.

The word "comprises" and/or "comprising" means that the corresponding feature and/or component is present, but it should be appreciated that presence or addition of one or more other features, components, and/or a group thereof is not excluded. Further, when not separately specified or not clear in terms of the context that a singular form is indicated, it should be construed that the singular form generally means "one or more" in the present specification and the claims.

Prior to describing detailed contents for carrying out the present disclosure, it should be noted that configurations not directly associated with the technical gist of the present disclosure are partially omitted without departing from the technical gist of the present disclosure. Further, terms or words used in the present specification and claims should be interpreted as meanings and concepts which match the technical spirit of the present disclosure based on a principle in which the inventor can define appropriate concepts of the terms in order to describe his/her invention by a best method.

The computer readable medium in the present specification may include all kinds of media storing programs and data so as to be readable by the computer system. The computer readable media in the present disclosure may include both "computer readable storage media" and "computer readable transmission media". According to an aspect of the present disclosure, the computer readable storage media may include a read only memory (ROM), a random access memory (RAM), a compact disk (CD)-ROM, a digital video disk (DVD)-ROM, a magnetic tape, a floppy disk, an optical data storage device, and the like. Further, the computer readable transmission media may include a predetermined medium of a type which is transmittable, which is implemented in a type of a carrier wave (e.g., transmissions through the Internet). Additionally, the computer readable media are distributed to systems connected through network to store computer readable codes and/or commands in a distribution scheme.

In this specification, "imaging", "photographing", and "scan" operations may be used exchangeably with each other and OCT data (i.e., OCT image) may be acquired by the operations.

Figure 1:
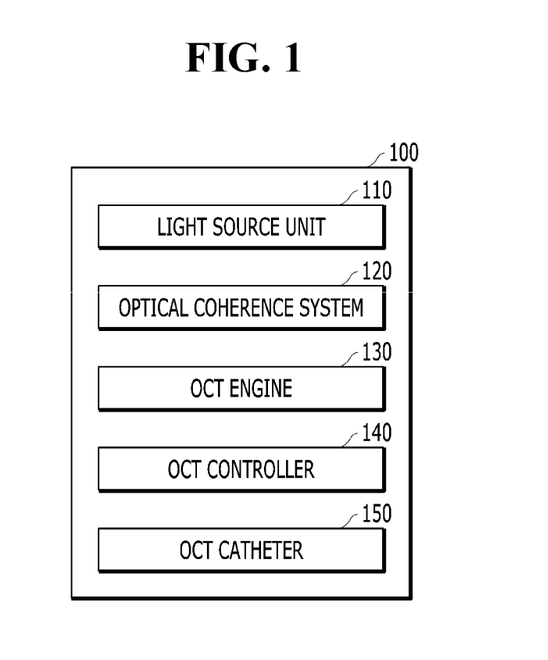
FIG. 1 is a schematic view of an OCT system according to an exemplary embodiment of the present disclosure.

FIG. 1 is a schematic view of an OCT system 100 according to an exemplary embodiment of the present disclosure.

As illustrated in FIG. 1, the OCT system 100 according to an exemplary embodiment of the present disclosure may include a light source unit 110, an optical coherence system 120, an OCT engine 130, an OCT controller 140, and an OCT catheter 150. The OCT system 100 may include a predetermined type of system using OCT technology and for example, an instrument, equipment, a device, an apparatus, a user terminal, a server, software, middle ware, and a combination thereof may constitute the OCT system 100. The OCT system 100 illustrated in FIG. 1 is exemplary and according to an implementation scheme, additional components may be included or some of the components may be omitted. For example, the OCT system 100 may be inserted into a blood vessel and may further include a guide wire (not illustrated) guiding the OCT catheter 150. As another example, the OCT system 1000 may further include an output unit such as a display (not illustrated) and/or an input unit such as a keyboard and a mouse (not illustrated).

The light source unit 110 may generate light used for imaging in the OCT system 100. For example, the light source unit 110 may generate and/or output two or more light having different wavelength bands or light having the same wavelength. When the light source unit 110 generates two or more different light, the light source unit 110 may combine two or more light and output one combination light. Additionally, the light source unit 110 may output the light by performing an operation of amplifying and filtering the generated light.

The optical coherence system 120 may include an optical coupler splitting the light generated by the light source unit 110 into first distribution light and second distribution light, a reference arm reflecting the first distribution light, a sample arm reflecting the second distribution light, and an optical detector detecting the light reflected by the reference arm and the sample arm. The optical coherence system 120 may use a coherence phenomenon in which two or more waves are different from the sum of original waves in a scheme in which two or more waves are strengthened or weakened when two or more waves overlap with each other. The optical coherence system 120 may move the first distribution light among the distributed light along a path depending on the reference arm and reflect the first distribution light through a reflector positioned at one end of the reference arm and move the second distribution light among the distributed light along the path depending on the sample arm and acquire light back-scattered by tissue adjacent to the sample arm. The optical coherence system 120 combines the reflected first distribution light and the back-scattered second distribution light by the optical detector to generate the combination light. The reflected first distribution light and the back-scattered second distribution light may cause mutual interference in the combination light. The coherence or a coherence signal may be transferred to the OCT engine 130 and processed. According to an additional exemplary embodiment, the optical coherence system 120 may further include an optical delayer delaying light and/or a polarizer polarizing light in a specific form.

The OCT catheter 150 has a shape in which the OCT catheter 150 is insertable into at least a part of a human body and includes an optical fiber which is rotatable and discharges the light to tissue and receives the light reflected from the issue to collect OCT data for the tissue. The OCT catheter 150 may include one or more optical fibers and may transfer the light to the tissue of the human body through a core and/or cladding structure and may include one or more lens structures at one end portion. One end portion of the OCT catheter 150 may be coupled to the OCT controller 140 and another end portion may be positioned in the vicinity of the tissue during surgery. The OCT catheter 150 may have a flexible material. For example, the OCT catheter 150 may include a sheath and an optical fiber which is flexible and bidirectionally rotatable and the optical fiber may transmit and collect light in a wavelength band of a predetermined range. In an additional exemplary embodiment, the OCT catheter 150 may make an ultrasound sub-system which may irradiate energy in a range of a specific frequency be included in the sheath.

The OCT engine 130 may include a processor and a storage unit and process the OCT data collected by the OCT catheter 150. The OCT engine 130 may include predetermined type of computing equipment. The storage unit may include, for example, a computer readable medium, a machine readable medium, and/or a processor readable medium. The storage unit may store predetermined data processed by the OCT engine 130. The storage unit may include one or more memories including a buffer cache. Here, the memory as a primary storage device directly accessed by the processor, such as a random access memory (RAM) including a dynamic random access memory (DRAM), a static random access memory (SRAM), etc., may mean a volatile storage device in which stored information is momentarily erased when power is turned off, but is not limited thereto. Additionally, the storage unit may include a separate database management system (DBMS) and/or a persistent storage. In this case, the persistent storage means a non-volatile storage medium which may consistently store predetermined data, such as a magnetic disk, an optical disk, and a magneto-optical storage device and a storage device based on a flash memory and/or a battery-backup memory. The persistent storage may communicate with the processor and the storage unit of another computing device through various communication means including a network unit.

The processor reads a program/software stored in the storage unit to allow the OCT engine 130 to perform operations according to the program/software. The processor may be constituted by one or more cores and may mean a predetermined type of processor including a central processing unit (CPU), a general purpose graphics processing unit (GPGPU), a tensor processing unit (TPU), and the like of the OCT engine 130.

The OCT engine 130 may control all operations of the OCT system 100. Further, the OCT engine 130 may process and digitalize the light or signal detected by the optical detector of the optical coherence system 120. Further, the OCT engine 130 implements image processing for the digitalized signal to generate an image to be output to a user. For example, the OCT engine 130 image-processes the acquired data to generate a 2D or 3D image. For example, the OCT engine 130 may perform correction for a distortion phenomenon of the acquired image.

Further, the OCT engine 130 determines a first intensity value for first OCT data collected by the OCT catheter 150, determines a second intensity value for second OCT data collected by the OCT catheter 150, and compares the first intensity value and the second intensity value to determine to automatically trigger a pull-back operation of the OCT controller 140. That is, the OCT engine 130 compares intensity values for image data collected by the OCT catheter 150 to sense that there is a change of a specific intensity or more. In this case, the OCT engine 130 may trigger the OCT controller 140 so as to start photographing by sensing that the time when the change occurs is a time when a contrast medium is injected into the blood vessel, for example. That is, when the contrast medium is input into the blood vessel, a brightness intensity may be abruptly changed as compared with a brightness in the blood vessel in an existing case where there is the blood. Accordingly, when the contrast medium enters the blood vessel, there is no blood in the blood vessel, and as a result, the time when there is no blood may be a most suitable time for photographing the inside of the blood vessel. Such a time may be automatically detected through OCT data analysis by the OCT engine 130, and as a result, the user need not manually manipulate the pull-back operation of the OCT controller 140, thereby maximizing user convenience. Additionally, the OCT engine 130 may determine whether to trigger an automatic pull-back operation of the OCT controller 140 based on determination information (e.g., information on the amount of blood, information on the quantity of contrast media, and/or temperature information) for whether there is blood sensed from a sensor attached to one end portion of the OCT catheter 150. In an additional exemplary embodiment, the OCT engine 130 analyzes the OCT data acquired by the OCT catheter 150 to determine a current state of blood as a static state (a state where there is no movement) or a dynamic state (a state where there is the movement). In general, a result for imaging is not good at the time when the blood moves by cardiac impulse. Accordingly, when the OCT engine 130 determines the time for the static state where there is no movement of the blood, triggering of the OCT controller 140 may be determined at the corresponding time. That is, the OCT engine 130 analyzes the OCT data collected by the OCT catheter 150 to determine whether there is a blood flow and when the OCT engine 130 determines that there is no blood flow, the OCT engine 130 may determine to automatically trigger the pull-back operation of the OCT controller 140. Through an auto-trigger technique of the aforementioned schemes, an error of imaging due to movement of the blood may be efficiently solved.

The OCT controller 140 may be connected to a proximal end of the OCT catheter 150 and control rotation of the OCT catheter 150. The OCT controller 140 performs the pull-back operation according to a user input or as a predetermined condition is satisfied to cause the rotation of the OCT catheter 150. At least a part of the OCT controller 140 rotates by generating rotational power to cause the OCT catheter 150 to rotate. The OCT controller 140 includes a stator and a rotator to generate magnet-driven power and may rotate by the magnet-driven power.

The OCT controller 140 may perform a bearing operation for the rotation by using air. The OCT controller 140 may support a rotating operation of the OCT catheter 150 by using air pressure. The OCT controller 140 may include an air supply unit therein or receive the air from the outside.

Figure 2:
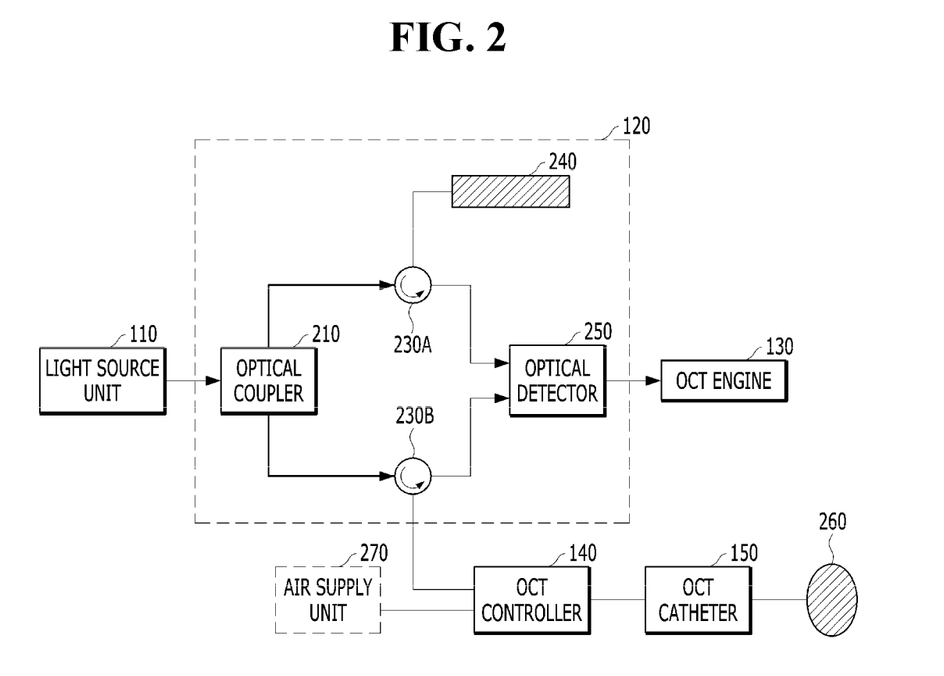
FIG. 2 is a block diagram for an OCT system according to an exemplary embodiment of the present disclosure.

FIG. 2 is a block diagram for an OCT system 100 according to an exemplary embodiment of the present disclosure.

As illustrated in FIG. 2, the optical coherence system 120 according to an exemplary embodiment of the present disclosure may include an optical coupler 210, a reference arm 220A, a first circulator 230A, a reflector 240, a sample arm 220B, a second circulator 230B, and an optical detector 250.

The light source unit 110 may generate light to be transferred to the optical coupler 210 of the optical coherence system 120. In an additional exemplary embodiment, the light source unit 110 may use dual wavelengths including light having different wavelengths. In this case, light having a wavelength band having high absorbance for a specific tissue and light having a wavelength band having low absorbance for the specific tissue are simultaneously used to more easily identify the specific tissue. As another example, the light source unit 110 may generate frequency tunable light.

The optical coupler 210 may split the light received from the light source unit 110 into first distribution light and second distribution light. The first distribution light may be transferred to the first circulator 230A along a path generated by the reference arm 220A. The first circulator 230A may transfer the light transferred along the path generated by the reference arm 220A to the reflector 240 and receive light reflected by the reflector 240 and transfer the light to the optical detector 250. Here, the reflector 240 may include a predetermined component or medium which may reflect light, such as a mirror. The second distribution light split by the optical coupler 210 may be transferred to the second circulator 230B along a path formed by the sample arm 220B. The second circulator 230B may transfer the light transferred along the path generated by the sample arm 220B toward the OCT controller 140 and receive back-scattered light from tissue 260 and transfer the light to the optical detector 250. In an exemplary embodiment, the light incident on the tissue 260 may be converged by an objective lens/collimator and incident on the tissue 260, for example. At least some of the light incident on the tissue 260 may be reflected and scattered and returned.

The optical detector 250 combines the light transferred from the first circulator 230A and the second circulator 230B to generate a coherence signal. The light combined by the optical detector 250 and/or coherence information may be input into the OCT engine 130 and processed by the OCT engine 130. For example, the OCT engine 130 may determine the coherence information from the combined light.

The OCT controller 140 is optically connected to the OCT catheter 150, and as a result, the image data collected by the OCT catheter 150 may pass through the OCT controller 140 and head toward the second circulator 230B. Since the OCT controller 140 may be connected to the air supply unit 270 in the OCT system 100, the OCT controller 140 may receive air for implementing an air bearing operation from the OCT system 100. Here, the air bearing operation may mean that a lubrication action for a rotary movement is implemented by the air.

That is, the OCT controller 140 according to an exemplary embodiment of the present disclosure may support the rotating operation of at least one of the OCT catheter 150 and the OCT controller 140 by using the air pressure. In this case, the OCT system 100 may further include an air supply unit 270 connected to the OCT controller 140 and providing the air pressure to the OCT controller 140.

The air supply unit 270 in FIG. 2 may be present inside or outside the OCT system 100 or may be provided in the OCT controller 140 itself.

In an exemplary embodiment, the air supply unit 270 may include an air compressor generating compressed air and transferring the generated compressed air to a cylinder and a cylinder providing a predetermined amount of air pressure to the OCT controller 140 based on the compressed air transferred from the compressor. That is, the air supply unit 270 in the OCT system 100 may include the air compressor and the cylinder.

In an exemplary embodiment of the present disclosure, the predetermined amount of air pressure may have a range of 10 to 200 psi. In another exemplary embodiment of the present disclosure, the predetermined amount of air pressure may have a range of 50 to 150 psi. Additionally, RPM of the rotation caused by the air bearing may be 500 to 100,000 RPM (in the case of 10 to 200 psi) or 20,000 to 60,000 RPM (in the case of 50 to 150 psi).

In the exemplary embodiment of the present disclosure, the air supply unit 270 may include an outside air inlet receiving outside air from the outside of the OCT system 100 and a cylinder providing a predetermined amount of air pressure to the OCT controller 140 by using the outside air transferred by the outside air inlet. That is, the OCT system 100 may receive the outside air from the air compressor positioned outside and supply the air to the OCT controller 140 by the cylinder included in the air supply unit 270 positioned inside the OCT system 100.

In an exemplary embodiment of the present disclosure, the air supply unit 270 may include a cylinder that receives the outside air from an air line connected to the OCT system 100 and provides the predetermined amount of air pressure to the OCT controller 140 by using the received outside air. That is, the OCT system 100 may receive the air through the air line from the outside and the air pressure may be provided to the OCT controller 140 by the cylinder included in the air supply unit 270 in the OCT system 100.

In an exemplary embodiment of the present disclosure, the OCT controller 140 may support at least one of the rotating operation of the OCT controller 140 and the rotating operation of the OCT catheter 150 by using the outside transferred from the air line connected to the OCT system 100.

Through the air bearing operation of the OCT controller 140, a radial error motion of the OCT controller 140 and/or the OCT catheter 150 does not exceed 0.1 micron. Furthermore, through the air bearing operation of the OCT controller 140, a tilt error motion of the OCT controller 140 and/or the OCT catheter 150 does not exceed 0.3 micron. Since the air bearing operation may reduce loss for the rotational power, high-speed rotation of the OCT controller 140 and/or the OCT catheter 150 may be implemented and reliability and accuracy of the rotation may be ensured. Additionally, as an air bearing technique is applied to the OCT controller 140, the necessity for maintenance (e.g., replacement) for the bearing operation may also be removed and system complexity of the OCT controller 140 may also further be reduced.

As an additional effect, a scanning time may be reduced through the air bearing operation, the distortion phenomenon of the image may be reduced with reduction of the scanning time, and a Saw artifact phenomenon may also be reduced as compared with the OCT controller controlled by a motor. Here, the Saw artifact phenomenon may mean a step phenomenon which is exemplarily illustrated in FIG. 12 and occurs in the acquired OCT data as a scanning start point and a scanning arrival point do not coincide with each other due to reasons including cardiac impulse during 360° rotation of the lens, a patient motion, instability of motor torque, etc.

Figure 3:
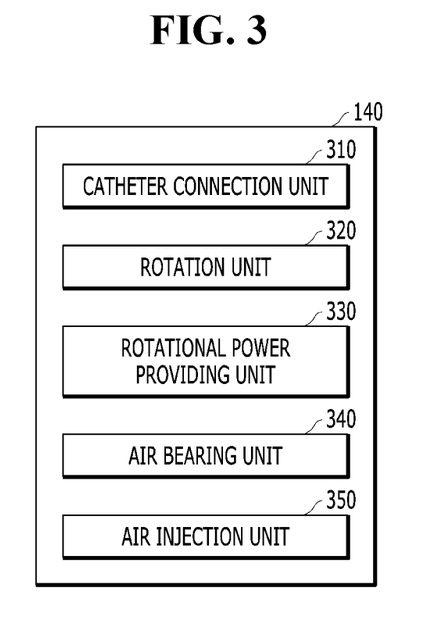
FIG. 3 illustrates an exemplary OCT controller in an OCT system according to an exemplary embodiment of the present disclosure.

FIG. 3 illustrates an exemplary OCT controller 140 in an OCT system 100 according to an exemplary embodiment of the present disclosure.

As schematically illustrated in FIG. 3, the OCT controller 140 may include a catheter connection unit 310 which may be coupled to the OCT catheter 150, a rotation unit 320 which autonomously rotates and transfers a rotary motion to the OCT catheter 150, a rotational power providing unit 330 which generates power for the rotary motion and transfers the generated power to the rotation unit 320, an air bearing unit 340 implementing the lubrication operation for the rotary motion, and an air injection unit 350 receiving the air from the outside of the OCT controller 140 and allowing the air bearing operation in the air bearing unit 340. The components of the OCT controller 140 are exemplary and additional components may exist or some of the components may be omitted.

The OCT controller 140 may include the catheter connection unit 310 detachably connected to the OCT catheter 150. The catheter connection unit 310 may have a shape in which the catheter connection unit 310 may be coupled to the proximal end of the OCT catheter 150. The catheter connection unit 310 may include a lock unit so as to prevent the coupled OCT catheter 150 from being decoupled. The catheter connection unit 310 may be rotatable in order to transfer the rotary motion to the OCT catheter 150 while being coupled to the OCT catheter 150. That is, the catheter connection unit 310 may be formed integrally with the rotation unit 320 and may rotate to correspond to the rotation of the rotation unit 320.

The OCT controller 140 may include the rotation unit 320 of which at least a part rotates to transfer the rotational power to the OCT catheter 150. The rotation unit 320 may implement a stable rotary motion through the air bearing operation by the air bearing unit 340.

The rotational power providing unit 330 includes the stator and the rotor to generate the magnet-driven power. The generated magnet-driven power is transferred to the rotation unit 320. As an additional exemplary embodiment, the rotational power providing unit 330 may generate the magnet-driven power and predetermined type of power.

The air bearing unit 340 may perform an air bearing operation of accommodating at least a part of the rotation unit 320 and injecting the air into a space formed between an inner surface and an outer surface of the accommodated rotation unit 320 and supporting the rotary motion of the rotation unit 320. In another exemplary embodiment, the air bearing unit 340 may mean a space of a form of surrounding the vicinity of the rotation unit 320. The air from the air injection unit 350 is injected into the space and the injected air may serve as a bearing supporting the rotation of the rotation unit 320.

The OCT controller 140 may implement the air bearing operation for the OCT catheter 150 through the air injection unit 350 which is accommodated in the OCT controller 140 and receives the air from the inside of the OCT system 100 or the outside of the OCT system 100. The air injection unit 350 may have a predetermined shape opening for injecting the air and may be at least partially opened/closed, and as a result, the air pressure may be adjusted according to opening/closing.

Figure 4:
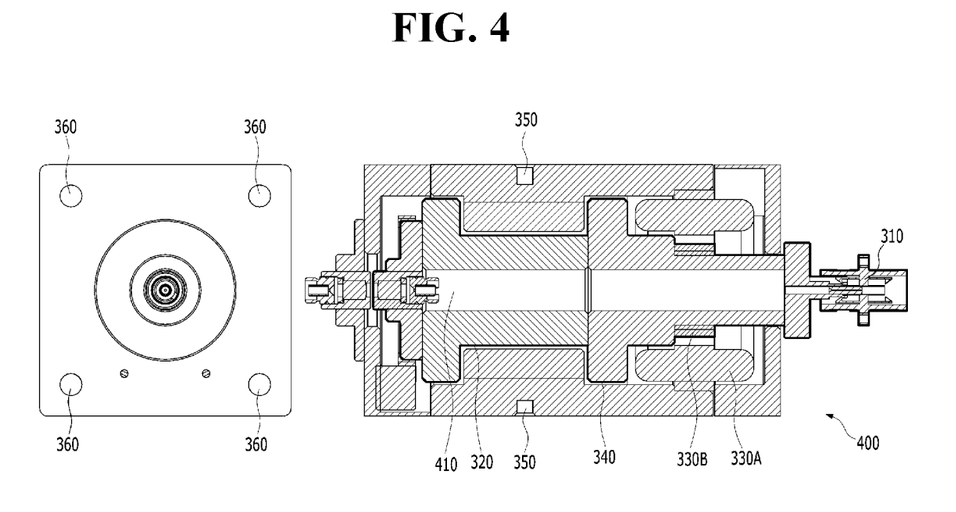
FIG. 4 exemplarily illustrates internal and external cross sections of an assembly structure of an OCT controller according to an exemplary embodiment of the present disclosure.

FIG. 4 exemplarily illustrates internal and external cross sections of an assembly structure 400 of an OCT controller 140 according to an exemplary embodiment of the present disclosure. The shape of the assembly structure 400 illustrated in FIG. 4 is exemplary and may be a predetermined different shape if functions according to the exemplary embodiments of the present disclosure are implemented.

The assembly structure 400 may be positioned inside the OCT controller 140 and at least a part rotates to cause the rotation of the OCT catheter 150.

A diagram illustrated at a left side in FIG. 4 is a cross section when the assembly structure 400 is viewed from the outside and a diagram illustrated at a right side in FIG. 4 is an internal cross-sectional view of the assembly structure 400.

Figure 5:
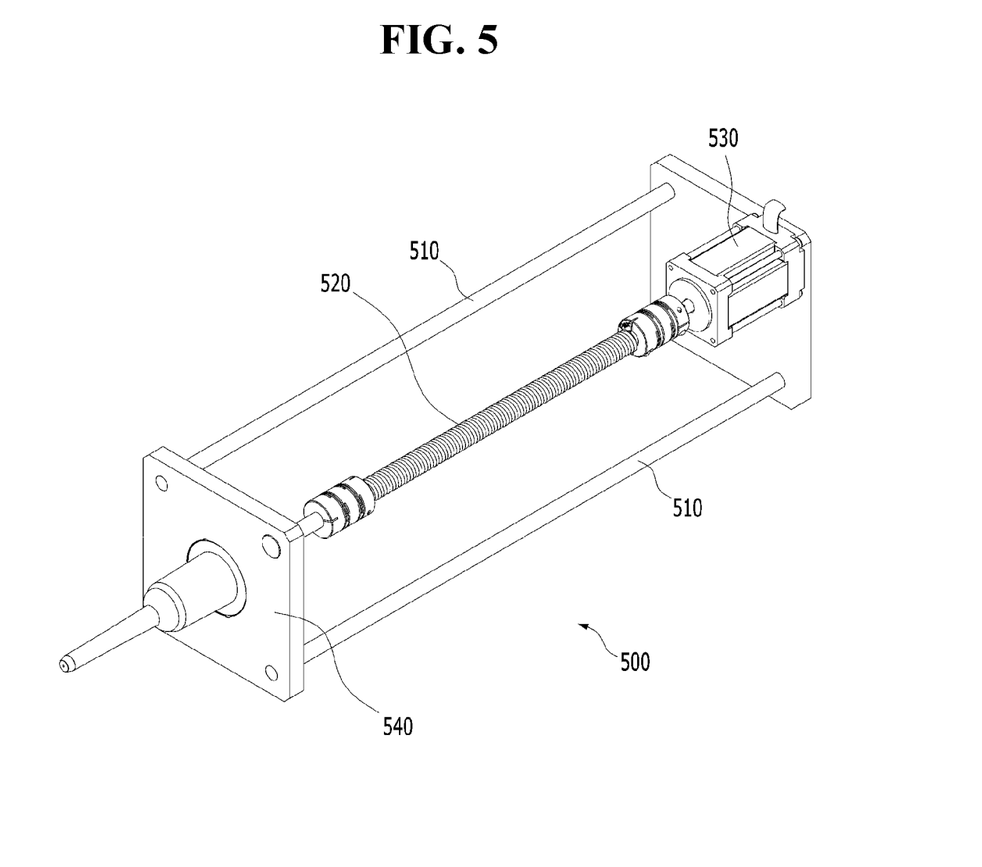
FIG. 5 exemplarily illustrates a perspective view for a pull-back structure of an OCT controller according to an exemplary embodiment of the present disclosure.

The assembly structure 400 may be accommodated in a housing of the OCT controller 140 while being coupled to a pull-back structure illustrated in FIG. 5.

According to an exemplary embodiment of the present disclosure, the assembly structure 400 may include an air injection unit 350 formed on one or more surfaces. The air injection unit 350 may have a shape to inject the air from the outside into the assembly structure 400.

The catheter connection unit 310 for coupling to the OCT catheter 150 may be formed at one end portion of the assembly structure 400. The catheter connection unit 310 may have a shape corresponding to the shape of the proximal end of the OCT catheter 150. The catheter connection unit 310 may have an opening having a size so as to insert the proximal end of the OCT catheter 150 into the inner surface of the catheter connection unit 310. An optical fiber(s) of the inserted OCT catheter 150 may be linked to an opposite end portion of the assembly structure 400 along a connection passage 410. The connection passage 410 is hollow and may not rotate.

One portion of the opposite end portion of the assembly structure 400 may be a non-rotation unit and the opposite end portion may receive the OCT data collected by the OCT catheter 150 through the optical fiber and transfer the OCT data to the OCT engine 130.

The assembly structure 400 may include the rotation unit 320. The rotation unit 320 may be disposed adjacent to the rotational power providing unit 330 including a drive rotator 330B and a drive stator 330A and rotated by rotational force generated by the rotational power providing unit 330. As illustrated in FIG. 4, the catheter connection unit 310 and the rotation unit 320 may be integrally formed and the rotation by the rotation unit 320 may be transferred to the OCT catheter 150.

As illustrated in FIG. 4, the assembly structure 400 may generate a space 340 which the air may enter in the vicinity of the rotation unit 320. The air from the air injection unit 350 is injected into the space 340 and a bearing function for the rotation of the rotation unit 320 may be performed. In an exemplary embodiment, the space 340 may mean an air bearing unit 340.

As illustrated in FIG. 4, the assembly structure 400 may include a plurality of linear bearing units 360 for coupling to the pull-back structure. For example, the linear bearing units 360 may have a tubular structure in a direction corresponding to a rotary axis of the rotation unit 320. The linear bearing units 360 serve as a bearing which allows the assembly structure 400 to be coupled to the pull-back structure and easily perform a translation motion. In FIG. 4, four linear bearing units 360 are exemplarily disclosed, but the number of linear bearing units 360 may be variable depending on the shape of the pull-back structure.

As illustrated in FIG. 4, the assembly structure 400 may include the catheter connection unit 310 detachably connected to the proximal end of the OCT catheter 150, include the rotation unit 320 which is formed integrally with the catheter connection unit 310 and of which at least a part rotates to guide rotation of the OCT catheter 150, include the rotational power providing units 330A and 330B disposed adjacent to at least a part of an outer peripheral surface of the rotation unit 320 and providing the rotational power to the rotation unit 320, and include the air bearing unit 340 forming a space supporting the rotary motion of the rotation unit 320 by injecting the supplied air into the outer surface of the rotation unit 320.

FIG. 5 exemplarily illustrates a perspective view for a pull-back structure 500 of an OCT controller 140 according to an exemplary embodiment of the present disclosure.

As illustrated in FIG. 5, the pull-back structure 500 is coupled to the assembly structure 400 described in FIG. 4 to cause a linear translation motion of the assembly structure 400. As a result depending on the linear translation motion, the pull-back operation of the OCT controller 140 may be performed.

That is, the OCT controller 140 may further include a pull-back structure 500 which is coupled to the assembly structure 400 to cause the linear motion of the assembly structure 400, thereby implementing the pull-back operation of the OCT controller 140. The pull-back structure 500 coupled to the assembly structure 400 may be positioned in the housing of the OCT controller 140.

In an exemplary embodiment of the present disclosure, the pull-back structure 500 may include linear guide lines 510 inserted into the linear bearing units 360 of the assembly structure 400, respectively. That is, the linear guidelines 510 may couple the assembly structure 400 and the pull-back structure 500 in a scheme in which the linear guidelines 510 pass through the insides of the linear bearing units 360 formed at corresponding locations of the assembly structure 400, respectively. The linear guideline 510 may be formed in a direction corresponding to the direction of the rotary axis of the rotation unit 320. The linear guideline 510 may serve to strengthen coupling between the assembly structure 400 and the pull-back structure 500.

The pull-back structure 500 may include a linear power providing unit 530 that generates power for the linear motion of the assembly structure 400. The linear power providing unit 530 may include a predetermined type motor capable of generating the power. The pull-back structure 500 may include a worm 520 which is connected to the linear power providing unit 530 and rotated by the power generated by the linear power providing unit. In an exemplary embodiment, the worm 520 may have a screw type external surface. Further, the worm 520 may be coupled to the linear bearing unit 360 formed at the corresponding location in the assembly structure 400 and in this case, the corresponding linear bearing unit 360 may include a worm gear (not illustrated) which is engaged and coupled with the screw type external surface of the worm 520. Accordingly, the worm gear may convert the rotary motion of the worm 520 into the linear motion of the assembly structure 400. That is, with the rotary motion of the worm 520, the assembly structure 400 performs the linear translation motion, and as a result, the pull-back operation may be implemented. In an exemplary embodiment, while the pull-back operation is performed, as the rotation unit 320 of the assembly structure 400 rotates, a cross-sectional image for a tissue in a specific range may be acquired.

A predetermined scheme lock mechanism 540 for preventing the OCT catheter 150 from being decoupled after the OCT catheter 150 is coupled may be formed at an end portion close to the OCT catheter 150 of the pull-back structure 500.

Figure 6:
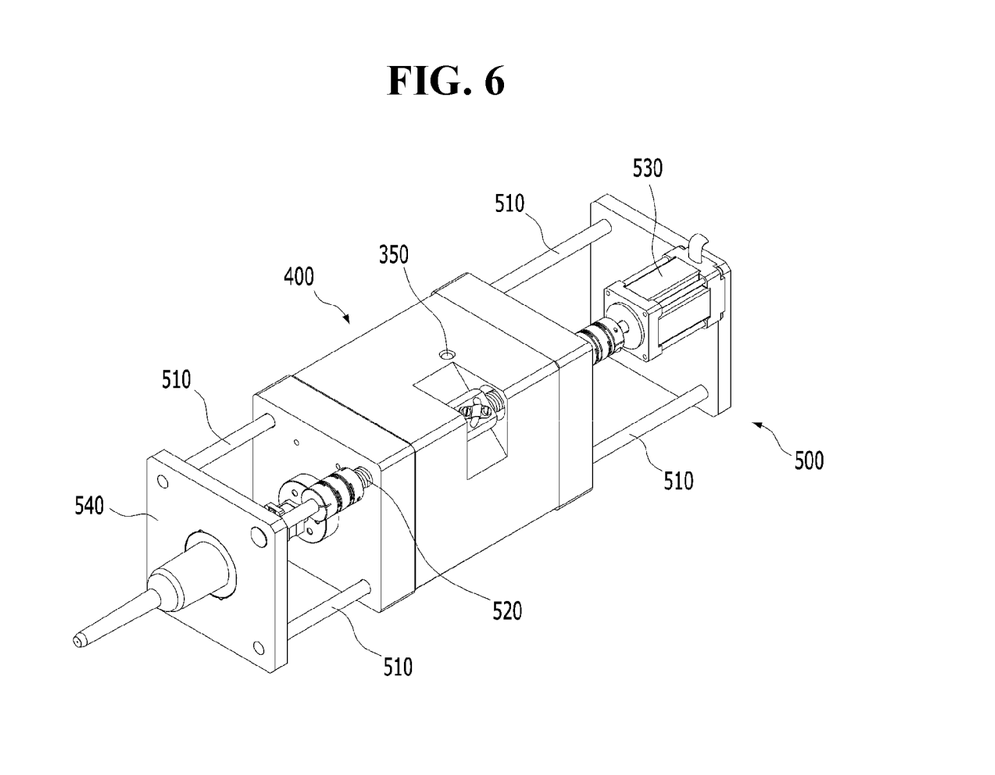
FIG. 6 exemplarily illustrates a perspective view for a coupling state of an assembly structure and a pull-back structure which may be accommodated in a housing of an OCT controller according to an exemplary embodiment of the present disclosure.

FIG. 6 exemplarily illustrates a perspective view for a coupling state of an assembly structure 400 and a pull-back structure 500 which may be accommodated in a housing of an OCT controller 140 according to an exemplary embodiment of the present disclosure.

As illustrated in FIG. 6, the coupled structures may implement the pull-back operation. As described above, the worm 520 rotates by the power generated by the linear power providing unit 530 and the worm gear coupled to the worm 520 which rotates causes the translation motion of the assembly structure 400. The rotation unit 320 of the assembly structure 400 rotates together with the translation motion and the OCT catheter 150 rotates by the rotation and the OCT data for the tissue may be collected by a lens structure positioned at a distal end of the OCT catheter 150. The air injected by the air injection unit 350 may serve as the bearing for the rotary motion of the rotation unit 320.

Figure 7:
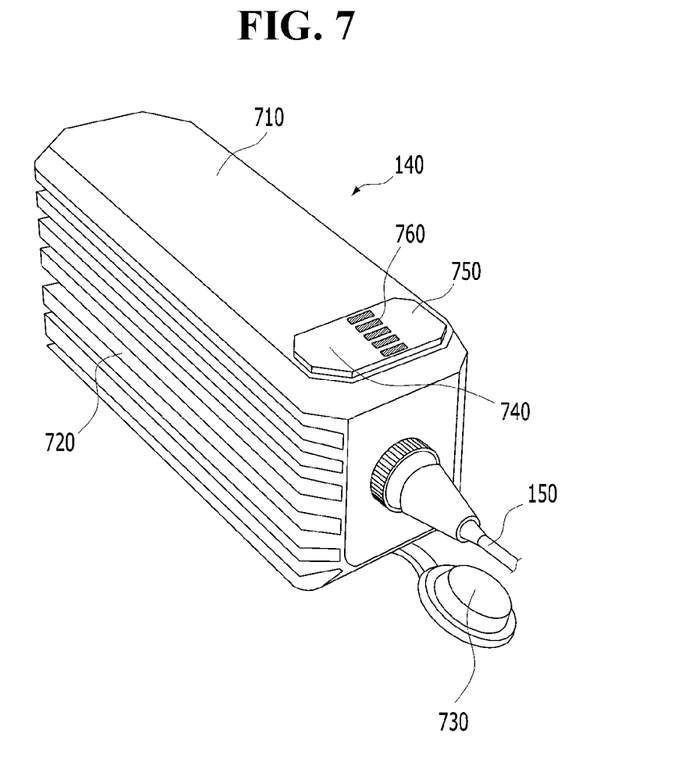
FIG. 7 is a perspective view exemplarily illustrating an OCT controller according to an exemplary embodiment of the present disclosure.

FIG. 7 is a perspective view exemplarily illustrating an OCT controller 140 according to an exemplary embodiment of the present disclosure.

The OCT controller 140 illustrated in FIG. 7 includes a housing 710 forming a space which may accommodate the assembly structure and the pull-back structure therein. The housing 710 may be made of a material such as plastic, metal, and/or rubber. A plurality of concave grooves 720 formed in a longitudinal direction of the OCT controller 140 may be formed on one or more lateral surfaces of the housing 710 in order to protect the housing 710 from external force and enhance a grip sense of the housing 710. One or more ventilation openings through which the air in the housing 710 may be ejected to the outside may be formed at some portions of the concave grooves 720, and as a result, some of the air used for implementing the air bearing operation may be ejected to the outside.

The concave grooves 720 may be formed on a lower surface (e.g., a bottom portion) of the OCT controller 140. In this case, an OCT controller docking unit (not illustrated) in the OCT system 100 may include concave portions or convex portions having a shape corresponding to the concave grooves 720, and as a result, the OCT controller 140 may be easily docked to the OCT system 100 while both concave portions are engaged and coupled. Accordingly, when the OCT controller 140 is coupled to the OCT system 100, friction force and/or a friction area of the coupling may increase so that the OCT controller 140 is not easily decoupled from the OCT system 100.

As illustrated in FIG. 7, a cover unit 730 for preventing the opening of the catheter connection unit formed in the housing 710 from being exposed to the outside while not being connected to the OCT catheter 150 may be formed on a surface in the housing 710, which is connected to the OCT catheter 150. When a surface contacting the opening of the catheter connection unit among the surfaces of the cover unit 730 is coupled to the opening of the catheter connection unit, the surface may have a shape for sealing the opening of the catheter connection unit.

A stop button 740 for stopping the operation of the OCT controller 140 and an unload button 750 for unloading the OCT catheter 150 may be formed on one surface (e.g., a planar portion) of the housing 710. Further, a state indicator (e.g., LED) for displaying an operation state and/or a battery state of the OCT controller 140 may be additionally formed on the corresponding surface of the housing 710.

Figure 8:
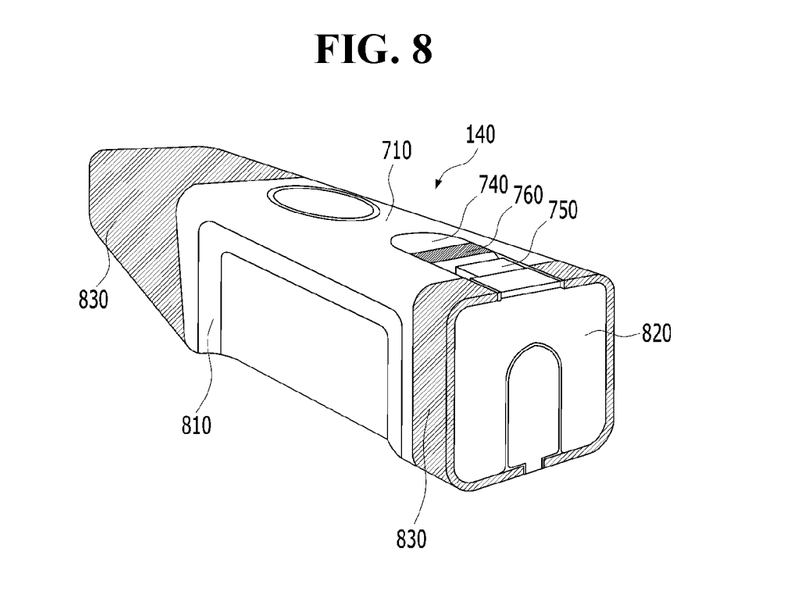
FIG. 8 is a perspective view exemplarily illustrating an OCT controller according to another exemplary embodiment of the present disclosure.

FIG. 8 is a perspective view exemplarily illustrating an OCT controller 140 according to another exemplary embodiment of the present disclosure.

As illustrated in FIG. 8, at least some of one or more surfaces (e.g., both lateral surfaces) in the housing 710 of the OCT controller 140 may have a tapered shape 810 in order to protect the housing 710 from the external force and enhance the grip sense of the housing 710.

As illustrated in FIG. 8, at least a part of the housing 710 of the OCT controller 140 may be made of an elastic material 830 for mitigating an impact from the outside.

The housing 710 may include a catheter engagement unit 820 which is formed to be connected onto one surface of the housing 710 and pivots between an opening location and a closing location. A detailed operation of the catheter engagement unit 820 will be described below in FIG. 11.

As exemplarily illustrated in FIG. 8, a stop button 740 for stopping the operation of the OCT controller 140 and an unload button 750 for unloading the OCT catheter 150 may be formed on one surface (e.g., a planar portion) of the housing 710. Further, a state indicator (e.g., LED) for displaying an operation state and/or a battery state of the OCT controller 140 may be additionally formed on the corresponding surface of the housing 710.

Figure 9:
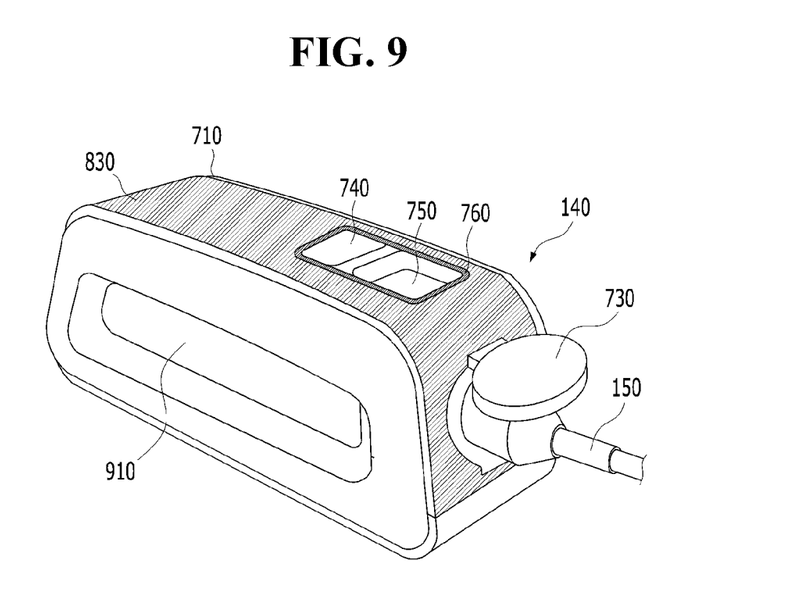
FIG. 9 is a perspective view exemplarily illustrating an OCT controller according to another exemplary embodiment of the present disclosure.

FIG. 9 is a perspective view exemplarily illustrating an OCT controller 140 according to another exemplary embodiment of the present disclosure.

At least one lateral surface of the housing 710 may have a shape 910 in which a width of a center is smaller than those of end portions of the lateral surface, in order to protect the housing 710 from the external force and/or enhance the grip sense of the housing 710. That is, since one portion on at least one surface of the housing 710 may have a recessed concave shape 910 as compared with other portions, a user may easily grip one portion of the housing 710 with a hand and the impact from the outside may be mitigated.

As illustrated in FIG. 9, at least a part of the housing 710 of the OCT controller 140 may be made of an elastic material 830 for mitigating an impact from the outside.

As exemplarily illustrated in FIG. 9, a stop button 740 for stopping the operation of the OCT controller 140 and an unload button 750 for unloading the OCT catheter 150 may be formed on one surface (e.g., a planar portion) of the housing 710. As exemplarily illustrated in FIG. 9, in order to increase a utilization degree of the stop button 740 in an emergency situation, the unload button 750 may be formed in a concave shape and the stop button 740 may be formed to be exposed to the outside so as to be easily pressed by the user. Further, a state indicator (e.g., LED) for displaying an operation state and/or a battery state of the OCT controller 140 may be additionally formed on the corresponding surface of the housing 710.

As illustrated in FIG. 9, a cover unit 730 for preventing the opening of the catheter connection unit formed in the housing 710 from being exposed to the outside while not being connected to the OCT catheter 150 may be formed on a surface in the housing 710, which is connected to the OCT catheter 150. When a surface contacting the opening of the catheter connection unit among the surfaces of the cover unit 730 is coupled to the opening of the catheter connection unit, the surface may have a shape for sealing the opening of the catheter connection unit.

Figure 10:
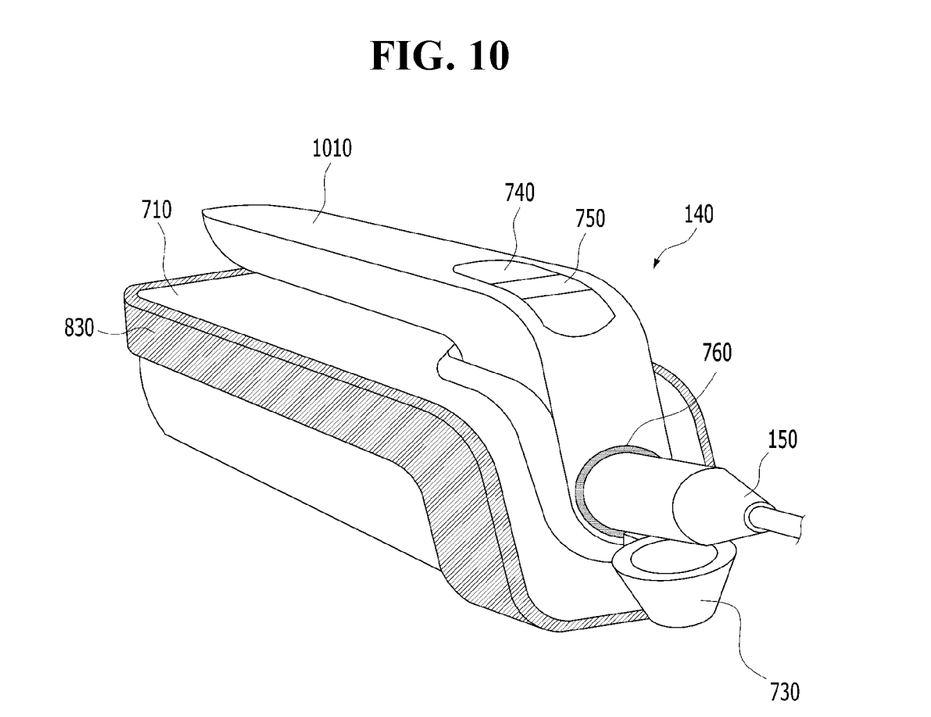
FIG. 10 is a perspective view exemplarily illustrating an OCT controller according to another exemplary embodiment of the present disclosure.

FIG. 10 is a perspective view exemplarily illustrating an OCT controller 140 according to another exemplary embodiment of the present disclosure.

A handle unit 1010 may be formed in the housing 710 of the OCT controller 140 in order to enhance manipulation easiness of the user. For example, the OCT controller 140 may be formed on one surface of the housing 710 and may include a handle unit 1010 which has a gap from the planar portion of the housing 710 as being formed in the longitudinal direction of the OCT controller 140.

As exemplarily illustrated in FIG. 10, a stop button 740 for stopping the operation of the OCT controller 140 and an unload button 750 for unloading the OCT catheter 150 may be formed on one surface (e.g., a planar portion) of the housing 710. Further, a state indicator (e.g., LED) for displaying an operation state and/or a battery state of the OCT controller 140 may be additionally formed on the corresponding surface of the housing 710.

As illustrated in FIG. 10, a cover unit 730 for preventing the opening of the catheter connection unit formed in the housing 710 from being exposed to the outside while not being connected to the OCT catheter 150 may be formed on a surface in the housing 710, which is connected to the OCT catheter 150. When a surface contacting the opening of the catheter connection unit among the surfaces of the cover unit 730 is coupled to the opening of the catheter connection unit, the surface may have a shape for sealing the opening of the catheter connection unit.

As illustrated in FIG. 10, at least a part of the housing 710 of the OCT controller 140 may be made of an elastic material 830 for mitigating an impact from the outside.

Figure 11:
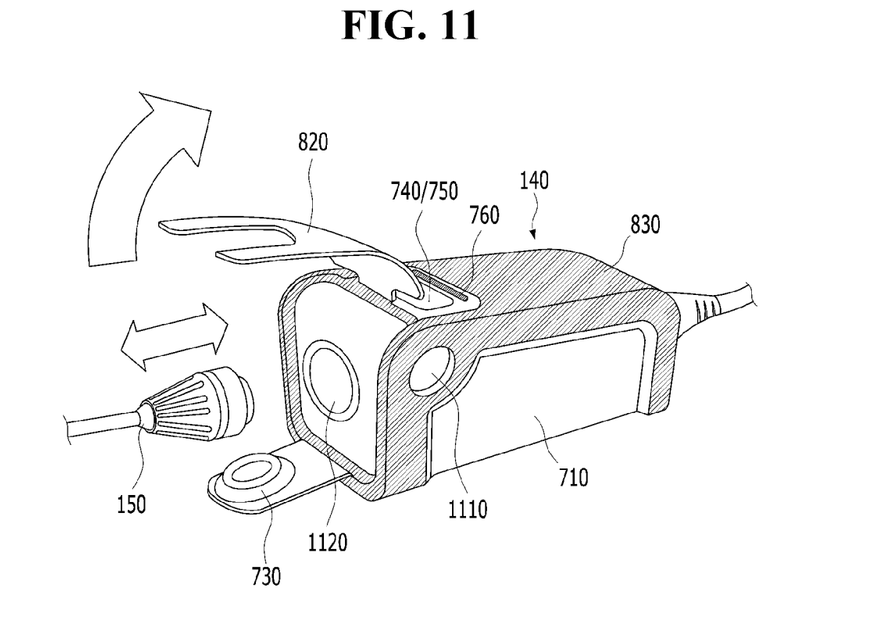
FIG. 11 is a perspective view exemplarily illustrating an OCT controller according to another exemplary embodiment of the present disclosure.

FIG. 11 is a perspective view exemplarily illustrating an OCT controller 140 according to another exemplary embodiment of the present disclosure.

As illustrated in FIG. 11, a cover unit 730 for preventing the opening 1120 of the catheter connection unit formed in the housing 710 from being exposed to the outside while not being connected to the OCT catheter 150 may be formed on a surface in the housing 710, which is connected to the OCT catheter 150. When a surface contacting the opening 1120 of the catheter connection unit among the surfaces of the cover unit 730 is coupled to the opening 1120 of the catheter connection unit, the surface may have a shape for sealing the opening 1120 of the catheter connection unit.

The opening 1120 for exposing the catheter connection unit to the outside may be formed in the housing 710 so that the OCT catheter 150 is input into the OCT controller 140 and the housing 710 may include a catheter engagement unit 820 which is formed to be connected onto one surface of the housing 710 and pivots between the opening location and the closing location. The catheter engagement unit 820 includes a fixation end fixedly coupled onto one surface of the housing 710 and a free end having a groove formed to be concave toward the fixation end and when the catheter engagement unit 820 pivots from the opening location to the closing location while the OCT catheter 150 is coupled to the catheter connection unit, decoupling between the OCT catheter 150 and the catheter connection unit may be prevented. That is, a size of the groove of the catheter engagement unit 820 may be smaller than a cross-sectional area of the proximal end of the OCT catheter 150. Further, an opening/closing control unit 1110 for controlling movement to the opening location and the closing location of the catheter engagement unit 820 may be provided at one portion of the housing 710.

As exemplarily illustrated in FIG. 11, a stop button 740 for stopping the operation of the OCT controller 140 and an unload button 750 for unloading the OCT catheter 150 may be formed on one surface (e.g., a planar portion) of the housing 710. Further, a state indicator (e.g., LED) for displaying an operation state and/or a battery state of the OCT controller 140 may be additionally formed on the corresponding surface of the housing 710.

As illustrated in FIG. 11, at least a part of the housing 710 of the OCT controller 140 may be made of an elastic material 830 for mitigating an impact from the outside.

Figure 12:
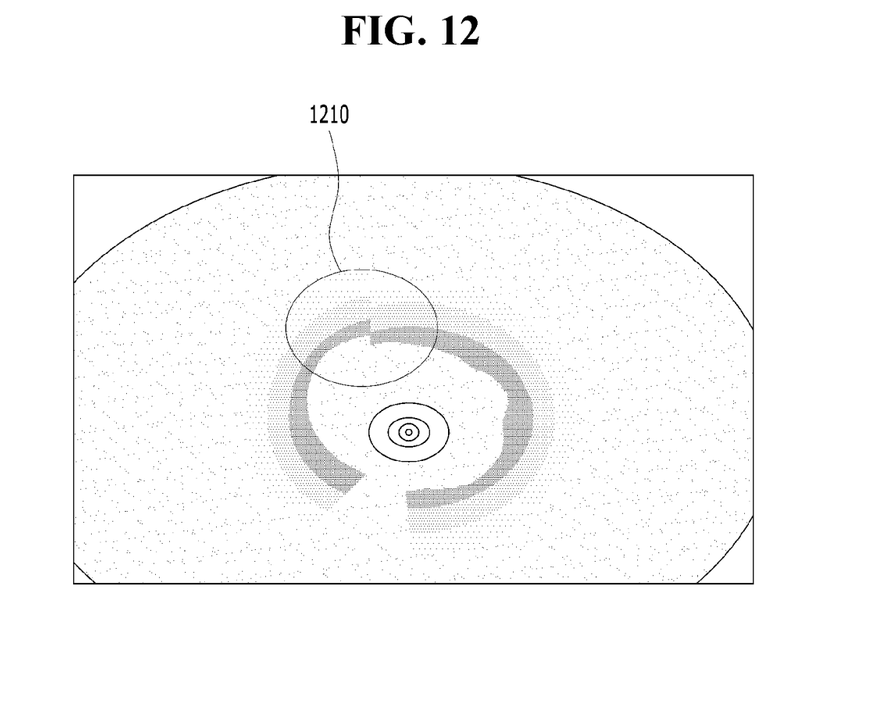
FIG. 12 exemplarily illustrates Saw Artifact mentioned in the present disclosure.

FIG. 12 exemplarily illustrates Saw Artifact mentioned in the present disclosure.

According to an exemplary embodiment of the present disclosure, a scanning time may be reduced through the air bearing operation, the distortion phenomenon of the image may be reduced with reduction of the scanning time, and a Saw artifact phenomenon 1210 may also be reduced as compared with the OCT controller controlled by a motor. The Saw artifact phenomenon in this specification may mean a step phenomenon 1210 which is exemplarily illustrated in FIG. 12 and occurs in the acquired OCT data as a scanning start point and a scanning arrival point do not coincide with each other due to reasons including cardiac impulse during 360° rotation of the lens of the OCT catheter 150, a patient motion, instability of motor torque, etc.

According to an exemplary embodiment of the present disclosure, the saw artifact phenomenon is reduced, and as a result, a more accurate OCT image may be provided to the user. Further, since the accurate OCT image may be acquired, a separate additional process for processing an OCT image in the OCT engine may also be reduced.

It will be appreciated that a specific order or a hierarchical structure of steps in the presented processes is one example of exemplary accesses. It will be appreciated that the specific order or the hierarchical structure of the steps in the processes within the scope of the present disclosure may be rearranged based on design priorities. Appended method claims provide elements of various steps in a sample order, but it does not mean that the method claims are limited to the presented specific order or hierarchical structure.

The description of the presented embodiments is provided so that those skilled in the art of the present disclosure use or implement the present disclosure. Various modifications of the embodiments will be apparent to those skilled in the art and general principles defined herein can be applied to other embodiments without departing from the scope of the present disclosure. Therefore, the present disclosure is not limited to the embodiments presented herein, but should be analyzed within the widest range which is coherent with the principles and new features presented herein.

What is claimed is:

1. An optical coherence tomography (OCT) system comprising:
 a light source unit generating light;
 an optical interferometer including an optical coupler splitting the light generated by the light source unit into first distribution light and second distribution light, a reference arm reflecting the first distribution light, a sample arm reflecting the second distribution light, and an optical detector detecting the light reflected by the reference arm and the sample arm;
 an OCT catheter including an optical fiber which has a shape in which the optical fiber is insertable into at least a part of a human body and which is rotatable and discharging the light to a tissue and collecting OCT data for the tissue;
 an OCT engine including a processor and a storage unit and processing the OCT data collected by the OCT catheter; and
 an OCT controller connected to a proximal end of the OCT catheter and controlling rotation of the OCT catheter,
 wherein the OCT controller supports a rotating operation of at least one of the OCT catheter and the OCT controller by using air pressure.

2. The OCT system of claim 1, further comprising:
an air supply unit connected to the OCT controller and providing air pressure to the OCT controller.

3. The OCT system of claim 2, wherein the air supply unit includes:
an air compressor generating compressed air and transferring the generated compressed air to a cylinder; and
a cylinder providing a predetermined amount of air pressure to the OCT controller based on the compressed air transferred from the air compressor.

4. The OCT system of claim 2, wherein the air supply unit includes:
an outside air inlet receiving outside air from the outside of the OCT system; and
a cylinder providing a predetermined amount of air pressure to the OCT controller based on the outside air transferred by the outside air inlet.

5. The OCT system of claim 2, wherein the air supply unit includes a cylinder receiving the outside air from an air line connected to the OCT system and providing the predetermined amount of air pressure to the OCT controller by using the received outside air.

6. The OCT system of claim 1, wherein the OCT controller supports the rotating operation of the OCT catheter by using the outside air received from the air line connected to the OCT system.

7. The OCT system of claim 1, wherein the OCT controller includes:
a catheter connection unit detachably connected to the OCT catheter;
a rotation unit of which at least a part rotates to transfer rotational power to the OCT catheter; and
an air bearing unit accommodating at least a part of the rotation unit and injecting air into a space formed between an inner surface and an outer surface of the accommodated rotation unit to support a rotary motion of the rotation unit.

8. The OCT system of claim 1, wherein the OCT controller performs an air bearing operation for the OCT catheter through an air injection unit which is accommodated in the OCT controller and receives air from the inside of the OCT system or the outside of the OCT system.

9. The OCT system of claim 1, wherein a processor of the OCT engine is further configured to:
determine a first intensity value for first OCT data collected by the OCT catheter,
determine a second intensity value for second OCT data collected by the OCT catheter, and
compare the first intensity value and the second intensity value to determine to automatically trigger a pull-back operation of the OCT controller.

10. The OCT system of claim 1, wherein the processor of the OCT engine is further configured to:
analyze the first OCT data collected by the OCT catheter to determine whether there is a blood flow, and
determine to automatically trigger the pull-back operation of the OCT controller when determining that the blood flow does not exist.

11. The OCT system of claim 1, wherein the OCT controller includes:
a housing having an accommodation space formed therein; and
an assembly structure accommodated in the housing,
the assembly structure including:
a rotation unit which includes a catheter connection unit detachably connected to a proximal end of the OCT catheter and in which at least a part rotates to guide rotation of the OCT catheter;
a rotational power providing unit disposed adjacent to at least a part of an outer peripheral surface of the rotation unit and providing the rotational power to the rotation unit; and
an air bearing unit injecting air supplied to an outer surface of the rotation unit and forming a space supporting the rotary motion of the rotation unit.

12. The OCT system of claim 11, wherein the OCT controller further includes a pull-back structure coupled to the assembly structure and causing a linear motion of the assembly structure to implement a pull-back operation of the OCT controller, and
the pull-back structure includes:
at least one linear guide line passing through at least one linear bearing unit formed in the assembly structure and formed in a direction corresponding to a direction of a rotary axis of the rotation unit;
a linear power providing unit generating power for the linear motion of the assembly structure; and
a worm connected to the linear power providing unit and rotated by the power generated by the linear power providing unit, and
the assembly structure further includes a worm gear coupled to the worm and the worm gear converts the rotary motion of the worm into the linear motion of the assembly structure.

13. The OCT system of claim 11, wherein the rotational power providing unit includes a stator and a rotator and providing magnet-driven power to the rotation unit.

14. The OCT system of claim 11, wherein a plurality of concave grooves formed in a longitudinal direction of the OCT controller is formed on at least one lateral surface of the housing in order to protect the housing from external force and enhance a grip sense of the housing.

15. The OCT system of claim 11, wherein at least a part of at least one lateral surface of the housing has a tapered shape in order to protect the housing from external force and enhance a grip sense of the housing.

16. The OCT system of claim 11, wherein at least one lateral surface of the housing has a shape in which a width of a center is smaller than the widths of end portions of the lateral surface in order to protect the housing from the external force and enhance the grip sense of the housing.

17. The OCT system of claim 11, wherein the OCT controller further includes a handle unit provided on one surface of the housing and forming a gap from a planar portion of the housing as being formed in a longitudinal direction of the OCT controller.

18. The OCT system of claim 11, wherein an opening for exposing the catheter connection unit to the outside so that the OCT catheter is input is formed in the housing,
the housing includes a catheter engagement unit which is formed to be connected onto one surface of the housing and pivots between an opening location and a closing location, and
the catheter engagement unit includes a fixation end fixedly coupled onto one surface of the housing and a free end having a groove formed to be concave toward the fixation end and when the catheter engagement unit pivots from the opening location to the closing location while the OCT catheter is coupled to the catheter connection unit, decoupling between the OCT catheter and the catheter connection unit is prevented.

* * * * *